(12) United States Patent
Wolff et al.

(10) Patent No.: US 7,060,072 B2
(45) Date of Patent: Jun. 13, 2006

(54) MEDICAL TOOL

(75) Inventors: Wilhelm Wolff, Kitzbuhel (AT); Dov Klein, Savion (IL)

(73) Assignee: Karl Storz GmbH & Co. KG (DE)

( * ) Notice: Subject to any disclaimer, the term of this patent is extended or adjusted under 35 U.S.C. 154(b) by 296 days.

(21) Appl. No.: 10/247,176

(22) Filed: Sep. 19, 2002
(Under 37 CFR 1.47)

(65) Prior Publication Data
US 2003/0139747 A1    Jul. 24, 2003

(30) Foreign Application Priority Data
Sep. 20, 2001   (EP) .................................. 01122415

(51) Int. Cl.
*A61B 17/32* (2006.01)
(52) U.S. Cl. ........................................................ 606/84
(58) Field of Classification Search .................. 606/79, 606/84, 99, 100; 173/90, 112, 93; 30/168, 30/167, 2; 81/27
See application file for complete search history.

(56) References Cited

U.S. PATENT DOCUMENTS 3,568,657 A * 3/1971 Gue .............................. 125/40
4,697,586 A   10/1987 Gazale ......................... 128/92
6,174,311 B1  1/2001 Branch et al. ................ 606/61

FOREIGN PATENT DOCUMENTS

DE      19901047 A1 *  7/2000
EP       0 780 080 A1    6/1997
WO      WO 91/13536  *  9/1991

* cited by examiner

*Primary Examiner*—Eduardo C. Robert
*Assistant Examiner*—D. Jacob Davis
(74) *Attorney, Agent, or Firm*—St. Onge Steward Johnston & Reens LLC

(57) ABSTRACT

The invention relates to a medical instrument (1) for sectioning, removing, and particularly modeling bones, cartilage, and the like, in particular for a nasal bridge osteotomy, said instrument including a chisel (2) with a shaft (2*a*) and a chisel blade (2*b*) installed on the distal end of the shaft. A medical instrument (1) that allows easy and precise guidance of the chisel (2) is characterized, in accordance with the invention, by a handle (3) on which the chisel (2) can be secured for holding and guiding.

19 Claims, 2 Drawing Sheets

MEDICAL TOOL

Figure 1:
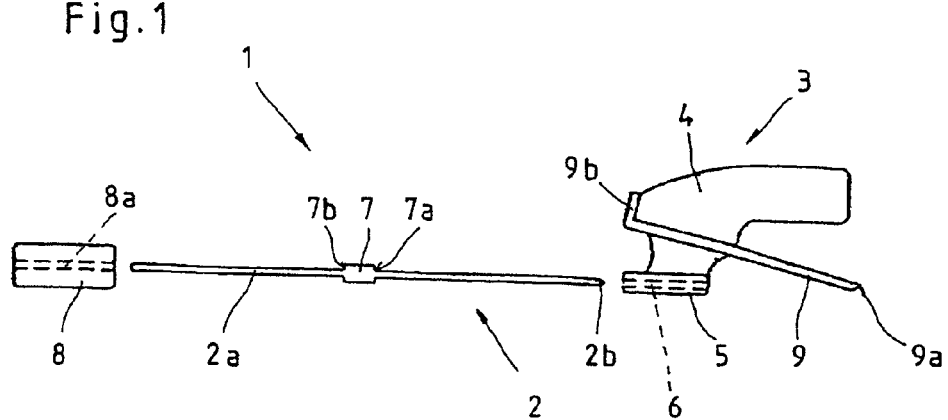

This application claims priority of pending European Patent Application No. 01 122415.1 filed Sep. 20, 2001.

FIELD OF THE INVENTION

The invention relates to a medical instrument for sectioning, removing, and particularly modeling bones, cartilage, and the like, in particular for a nasal bridge osteotomy, said instrument including a chisel with a shaft and a chisel blade installed on the distal end of the shaft.

Osteotomy is a surgical means of sectioning bones and the like with the help of a chisel or saw, for instance to correct malformations.

For osteotomy in the nasal bridge area, using customary operating techniques for the particular intended purpose, especially formed chisels are used which are propelled by a hammer. For this purpose the operator guides the chisel with one hand and strikes with the hammer held in the other hand against the proximal end of the chisel shaft opposite the chisel blade. The disadvantage of this familiar operating technique is that the chisel is guided directly by the operator's hand, even in applications such as the modeling of a nasal bridge in which extremely precise control of the chisel is required. When the chisel is propelled by the hammer, it can easily occur that the hand guiding the chisel becomes slightly displaced, which can result in a non-optimal treatment of the particular bone. Consequently, the invention addresses the task of preparing a medical instrument of the aforementioned type that allows simple and precise guidance of the chisel.

The solution of this task by means of the invention is characterized by a handle on which the chisel can be secured for holding and guiding.

For the first time, the use of the handle for the chisel makes it possible to guide the chisel, independently of the position, directly in the hand, especially in hammering. Placement of the chisel on the handle allows a simpler and firmer reception of the hammer blows without the risk, with each blow of the hammer, that the hand guiding the chisel could slip out of the position required for the particular cutting action.

In a practical embodiment of the invention, the handle includes a handle as well as a guide in which the chisel is placed. By means of the handle, the chisel placed in the guide can be brought simply and precisely into the desired working position and also during hammering can be brought into predetermined tracks proceeding from this position.

To ensure a firm, non-tiltable positioning of the chisel in the guide of the handle, an initial embodiment of the invention proposes that the guide is formed as a slit in a segment of the handle, so that the handle in this segment at least partially surrounds the cross-section of a segment of the chisel. In a second embodiment of the invention, the guide is formed as a guide device arranged in the handle, which device at least partially surrounds the cross-section of a segment of the chisel, so that the chisel is guided in the guide device. In particular in this embodiment, it is possible to move the chisel only sideways and in a turning motion around the chisel's longitudinal axis; on the other hand, however, this allows rotation around the chisel crosswise axis. In order to guide the chisel precisely and without any play in the hammering motion, the insertion depth of the chisel into the guide should preferably be a multiple of the height of the chisel's cross-section. For the parts of the chisel shaft as well as the guide, which form the glide pairing for displacing the chisel, it is preferably to use materials with good glide properties, in particular with a low friction coefficient, in order to ensure continuous secure sliding without any kind of chipping, even in an unfavorable position and under unfavorable working conditions.

To ensure, moreover, that the most diverse types of chisel, such as those with a straight, arched, or edged shaft, can be positioned precisely in the guide, the guide corresponds in longitudinal and cross-section to the longitudinal and cross-sectional shape of the segment of the chisel that is held in the guide.

It is further proposed, through the invention, that to limit the strike length of the chisel a stop is formed on the guide and/or on the chisel, so that the chisel can be struck only up to the desired point. The stop can be installed in such a way that it restricts the impact of the chisel either firmly or only reduces it.

In the design of the stop on the chisel, the stop is preferably configured as an enlargement of the cross-section of the chisel shaft in the area of the guide heading toward the handle or guide device, in such a way that this cross-section enlargement can be configured in the chisel main plane and/or in the plane perpendicular to this plane by the chisel's central axis and so that it forms a stop without any jamming effect.

In a preferred embodiment of the invention, especially for the open operating method, the chisel can be powered by means of a weight that can be slid onto the chisel's shaft in the working direction, so that a stop is configured on the chisel's shaft as an abutment for the weight. The impact of the chisel by means of the weight that works as a glide hammer and rests on the chisel's shaft ensures that the force applied by the hammer or weight on the chisel always acts exactly straight in the chisel direction. Sideways impact or even a sliding of the hammer is excluded by the construction of this particular shape. In addition, an instrument designed in this manner can be safely employed even in restricted spaces in which the use of a separate hammer is scarcely possible.

The weight that can be slid along the chisel's shaft as a glide hammer can consist of various materials and/or several parts of diverse substances. It is preferable to use materials tolerated by the body such as physically tolerable steel alloys, which can also be partially plastic coated.

In the selection of material, at least for the parts of the weight acting as a glide hammer, as well as of the chisel's shaft, which form the glide pairing for moving the weight along the chisel's shaft, preference is given to materials with good glide properties, in particular a low friction coefficient, to ensure a durably safe gliding without any kind of chipping By means of an ergonomically improved configuration of the external contour of the weight, the operator's action can be clearly improved and facilitated. This ergonomic design can, for instance, consist of the presence of gripping surfaces, so that diverse finger and hand sizes and shapes, as well as shapes for right and left handers, are possible. In addition to designing the ergonomic external contour by the addition of gripping surfaces, for instance, this ergonomic design can also be achieved if ergonomically improved components are secured to the weight, of material that can differ from that of the actual weight.

In order to keep production costs as low as possible for the configuration of the chisel that is preferred for the open operating method, it is also proposed that the stop that forms the abutment for the weight should, at the same time, also form the stop that limits the strike length of the chisel.

To protect the skin in the operating area, the invention proposes that a chisel blade protection be installed on the chisel in the area of the chisel blade, at least on one side and preferably on both sides, so that the chisel's blade can work only in the direction of operation.

In selecting material for the chisel blade protection, which can be made of various materials, particular care must be taken that materials are used which exclude any danger of injury to the operating personnel or to the patient's skin on the outside and, on the inside, exclude damage to the chisel or to the chisel blade protection, especially any chipping on one of the parts through possible touching with the chisel as the result of inadvertent shoving or striking.

In addition, the invention proposes that a soft-part protection be affixed on the handle to work as a retractor in order, on the one hand, to facilitate access to the operating area and on the other hand to protect surrounding tissue. The soft-skin protection can be designed to form a unit with the chisel blade protection, but it is also possible to configure the soft-part protection as a component that can be secured separately on the handle.

Precise guidance of the chisel, according to the invention, can be facilitated if an enclosure device can be secured on the handle to mark the end point for the chisel, which device should ideally have an impact stem to be secured to the end point, so that the body part to be operated on is secured by means of the enclosure device or the impact stem.

In a practical embodiment of the invention, the enclosure device marking the end point for the chisel also forms the soft-part protection serving as retractor.

It is also proposed, with the invention, that the enclosure device should have a hammer platform for striking the impact stem with a hammer that is separate from the chisel.

Finally, it is proposed with this invention that components, at least all those coming directly in contact with the patient's body, especially with bones and/or cartilage parts, should be produced from material that is tolerable for the body, particularly body-tolerable steel alloys. The parts of the instrument that are especially to be constructed from physically tolerable materials include primarily the chisel or at least the chisel blade, the soft-part protection, the enclosure device, and the impact stem, since these components not only come directly in contact with the patient's skin but also, in the case of open nasal bridge surgery, even touch exposed subcutaneous tissue and to some extent bones and cartilage parts.

Additional characteristics and advantages of the invention are demonstrated by the description of the related illustrations, which include merely schematic depictions of two models of a medical instrument in accordance with the invention. The illustrations are as follows:

FIG. 1 Lateral view of an initial embodiment of a medical instrument according to the invention, before the addition of individual parts.

Figure 2A:
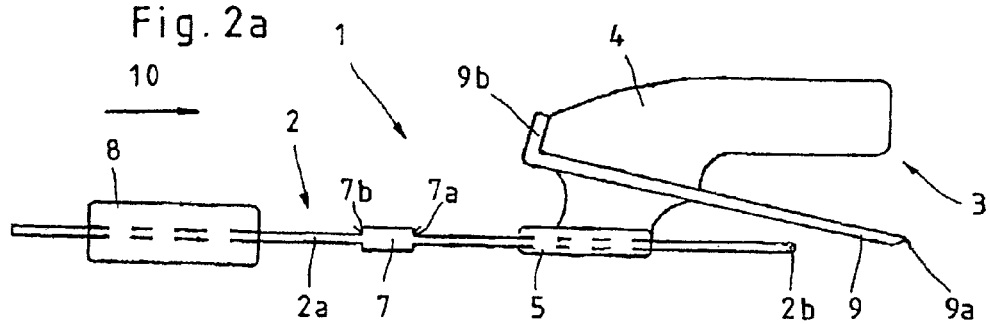

FIG. 2a Lateral view of the instrument in accordance with FIG. 1, in fully composed state, depicting an initial working position.

Figure 2B:
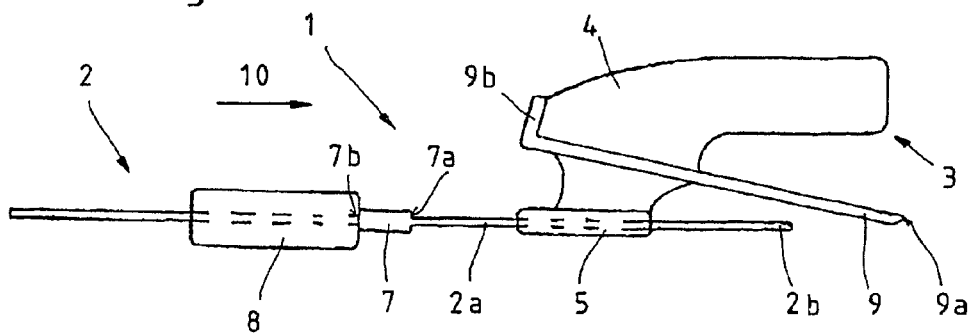

FIG. 2b A view as in FIG. 2a, but depicting a second working position.

Figure 3:
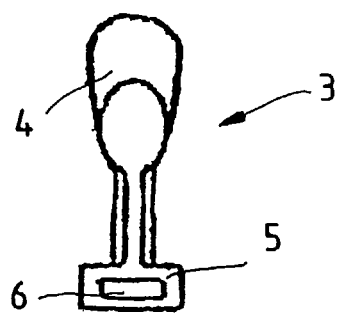

FIG. 3 Frontal view of the handle in accordance with FIG. 1.

Figure 4:
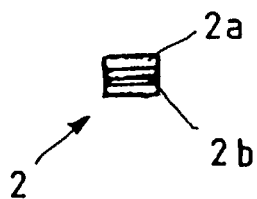

FIG. 4 Frontal view of the chisel in accordance with FIG. 1.

Figure 5:
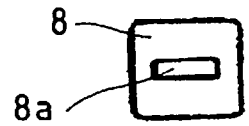

FIG. 5 Frontal view of the weight in accordance with FIG. 1.

Figure 6:
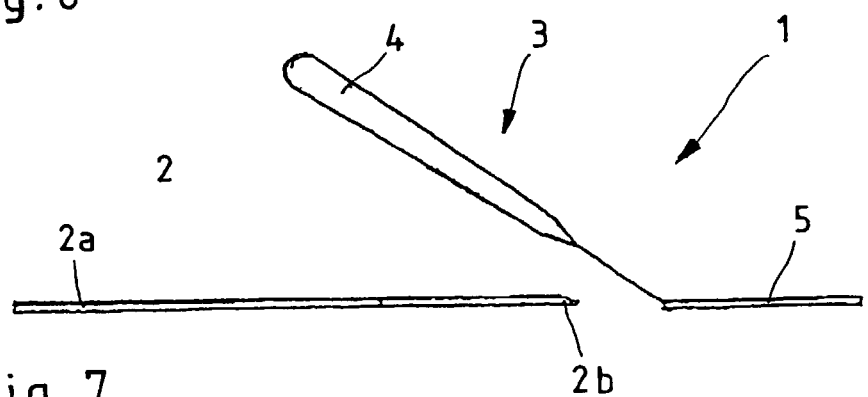

FIG. 6 Lateral view of a second model of a medical instrument according to the invention, before the addition of individual parts.

Figure 7:
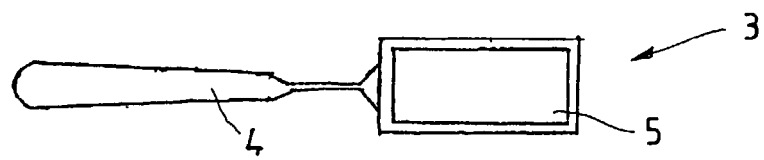

FIG. 7 Overview of the handle in accordance with FIG. 6.

Figure 8:
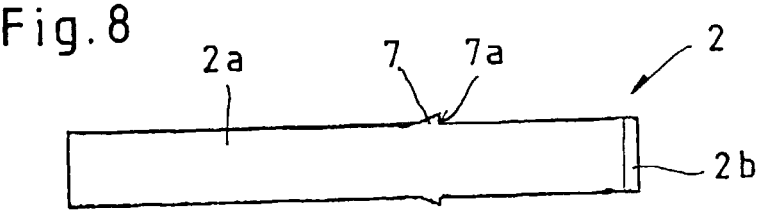

FIG. 8 Overview of the chisel in accordance with FIG. 6.

In the medical instruments illustrated in FIGS. 1, 2a, 2b, and 6 are employed in nasal bridge osteotomies, for instance for removing bone malformations in the nasal bridge area and for modeling the nasal bridge.

These medical instruments 1 consist essentially of a chisel 2 and a handle 3 for holding and guiding the chisel 2. The handle 3 in these illustrated models consists in each case of a grip 4 and a guide 5 securely fixed to the grip 4 and serving to receive the chisel 2.

The chisel 2, or at least the segment of the chisel 2 that comes directly in contact with the patient's body, that is, especially the chisel blade 2b, is preferably made up of a material tolerable to the body, for instance a bodily tolerable steel alloy.

As can be seen in particular from FIGS. 1 to 2b as well as FIG. 8, the chisel 2 consists of a shaft 2a, on whose distal end a chisel blade 2b is mounted which forms the actual tool. Contrary to the illustrated chisel 2 with a straight shaft 2a and a right-angle cross-section, there are also, depending on the intended purpose, chisels 2 with a rounded or edged longitudinal or cross-section, all of which can be secured onto a handle 3 for holding and guiding the chisel, in such a way that the guide 5 which receives the particular chisel 2 is adapted to the longitudinal and cross-section of the particular segment of the shaft 2a of the chisel 2, which is held in the guide 5. For guidance of the chisel 2 that exactly matches the position, it is therefore sufficient that the longitudinal and cross-section of the shaft 2a of the chisel 2 corresponds to the longitudinal and cross-section shape of the guide 5 in the area of the gliding guidance in the guide 5. In other areas, the longitudinal and cross-section shape of the shaft 2a of the chisel 2 can depart from the guide 5.

While the first embodiment shown in FIGS. 1 to 5 is used in the so-called open method, in which the operating area has first been prepared with surgical exactness, the nasal bridge osteotomy depicted in FIGS. 6 to 8 occurs in the so-called closed operating method, in which access to the operating area is through a nostril.

To ensure that the chisel 2 can be held and guided to the precise area and without tilting, the guide 5 in the first embodiment, illustrated in FIGS. 1 to 3, is configured as a slit 6 in one segment of the handle 3, so that the handle 3 in this segment at least partially surrounds the cross-section of the chisel 2 and the insertion depth for the shaft 2a of the chisel 2 is a multiple of the height of the shaft cross-section. As can be seen from FIG. 3, in this illustrated model the guide 5 has a circularly closed slit 6.

In the second model, illustrated in FIGS. 6 and 7, the guide 5 is configured as a guide device mounted on the handle 3, which device at least partially surrounds a segment of the chisel 2, so that the chisel 2 is guided in the guide device. In this model, which is preferred for the closed method, the guide 5 of the guide device surrounds the chisel 2, but only guides it laterally and in a turning motion around the chisel longitudinal axis. This allows a tilting of the chisel 2 around the chisel cross-axis and a slight motion of the chisel 2 upward and downward. Alternatively to the illustrated model, the guide device can also be configured in several parts and possibly detachable in such a way that it does not form a guide completely enclosing the chisel shaft, but merely forms a lateral turning guard, which also includes additional upper and lower guide and support glide guiding elements.

To limit the striking length of the chisel 2 in the illustrated models, a stop 7 is formed, increasing the cross-section of the shaft 2a, which stop contacts the guide 5 of the handle 3 with one stop surface 7a when the chisel 2 is driven forward, and thus restricts the strike path of the chisel 2. In the illustrated models the cross-section enlargement is configured by a widening of the chisel 2 in the chisel main plane. Alternatively or in addition, this cross-section enlargement may also be configured in the plane perpendicular to this plane. For various strike lengths, then, various chisels 2 are provided with stops 7 mounted accordingly.

It is also possible to configure the stop 7 to be adjustable on the chisel 2 for limiting the strike length. For this purpose the stop 7 can, for instance, take the form of a slit, adjusted to the shaft 2a of the chisel 2, in order to glide on it. Thus the stop 7 can be slid onto the shaft 2a of the chisel 2 and can be secured in one or various positions adjusted to the removal or operation purpose, for example by securing it by means of a screw in a groove.

In addition to configuring the stop 7 limiting the strike length of the chisel 2 on the shaft 2a, it is also possible of course to configure on the guide 5 a stop that works together with the shaft 2a.

The chisel 2 is driven in the working direction by means of a hammer. In the models illustrated in FIGS. 1 to 5, the hammer serving to drive forward the chisel 2 is configured as a weight 8 that is attachable on the shaft 2a of the chisel 2 and is movable along the shaft 2a. As can be seen in particular from FIG. 5, a guide slit 8a is configured in the weight 8 for sliding the weight 8 along the shaft 2a. The hammer force of this weight 8 working as a glide hammer on the chisel 2 is transmitted by means of a stop 7 formed on the shaft 2a of the chisel 2. As illustrated in FIGS. 2a and 2b, on sliding, the weight runs from the position in FIG. 2a into the position of FIG. 2b toward a stop surface 7b of the stop 7 and thus transmits the strike force to the chisel 2. In addition to the configured form in the illustration, in which the stop 7 for limiting the strike length of the chisel 2 and the stop 7, which serves as abutment for the glide hammer, meet, it is also possible to form two separate stops on the shaft 2a of the chisel 2. In the second configuration form illustrated in FIGS. 6 to 8, the chisel 2 is driven forward by means of a separate hammer, with which the operator strikes on the end of the shaft 2a opposite the chisel blade 2b. It is also possible, of course, with this medical instrument 1, to replace the separate hammer by a glide hammer configured as a slidable weight 8, as was described concerning the first embodiment of the medical instrument 1. For an exact fixing of the handle 3 bearing the chisel 2 in the area of the operation, the handle 3 has an enclosure device 9, whose distal end can be positioned precisely on the intended objective of the chisel 2. By means of a strike pin arranged on the distal end of the enclosure device 9, the enclosure device 9 can be secured against slipping, since a hammer platform 9b can be positioned on the proximal end of the enclosure device 9, by means of which the strike pin 9a can be secured with a hammer separate from the chisel 2 in the operating area. Penetration of the strike pin 9a into the bone or cartilage substance makes it necessary to select a bodily tolerable material for the strike pin 9a.

In the illustrated model, the enclosure device 9 also serves simultaneously as soft-part protection 9, which acts as a retractor to force tissue that is not to be treated away from the operating area. The advantage of this design is that the soft-part protection 9 cannot slip in chiseling thanks to the securing effect of the strike pin 9a of the enclosure device 9, and the target point for the chisel 2 is defined with exactitude. Even for the soft-part protection 9 designed here as a single unit with the enclosure device 9, it is essential that this protection, which comes in contact with the exposed subcutaneous tissue or with the internal skin layers, consist of material that is tolerable for the body.

As an additional protection for the patient, it is possible to arrange a non-illustrated chisel blade protection at least on one side but preferably on both sides in the area of the chisel blade 2b, in order to safeguard the patient's as well as the surgeon's skin against accidental injuries from the chisel blade 2b. The chisel blade protection can be configured by a particular shaping of the enclosure device 9 or can be mounted on the enclosure device 9 or on another segment of the handle 3. The medical instrument 1 as illustrated in FIGS. 1 to 6 is used as follows:

Starting with FIG. 1, the enclosure device 9 is first secured precisely to the target on the patient's previously freely prepared nasal bridge by the fact that the strike pin 9a is inserted in the nasal bridge by means of a hammer separate from the chisel 2 by way of the hammer platform 9b, so that the target point of the chisel 2 is determined exactly. Then the chisel 2 is inserted into the slit 6 of the guide 5. Upon striking the chisel 2, the weight 8 acting as a glide hammer is now slid onto the shaft 2a of the chisel 2 and is moved from the starting position shown in FIG. 2a in the direction of the arrow 10 until, as shown in FIG. 2b, the weight 8 engages the stop surface 7b of the stop 7 and thus the strike force of the weight 8 is transmitted to the chisel 2. The forward propulsion of the chisel 2 continues until the chisel 2 encounters the stop surface 7a of the stop 7 against the guide 5, so that the strike length of the chisel 2 is restricted. Now the strike pin 9a can again be withdrawn from the nasal bridge and the medical instrument 1 can be removed. It is also possible that the stop 7 is positioned with the stop surface 7a once again on the shaft 2a of the chisel 2, for instance by having a securing screw released from its groove and screwed into another groove, so that a new stop is achieved, which allows further opening of the nasal bridge.

The two illustrated embodiments of the medical instrument 1 are distinguished in that the chisel 2 is no longer required to be held directly by the operator's hand, but rather the chisel 2 is secured on the handle 3. By means of the handle 3, the operator can guide the chisel 2 much more safely and precisely than was previously possible.

REFERENCE LIST

1 Medical instrument
2 Chisel
2a Shaft
2b Chisel blade
3 Handle
4 Grip
5 Guide
6 Slit
7 Stop
7a Stop surface
7b Stop surface
8 Weight
8a Guide slit
9 Enclosure device/soft-part protection
9a Strike pin
9b Hammer platform
10 Arrow

What is claimed is:

1. Medical instrument for sectioning, removing, and particularly modeling bones, cartilage, and the like, said instrument including a chisel with a shaft and a chisel blade installed on the distal end of the shaft, said instrument further including a handle, on which the chisel is secured for holding and guiding, and wherein the handle includes a grip as well as a guide for receiving the chisel, said grip and said guide being set a distance apart from one another, and distinguished in that an enclosure device is secured onto the handle for marking a target point of the chisel and the enclosure device has a strike with a distal tip extending in a longitudinal direction of the enclosure device for penetrating into the objective in the longitudinal direction thereof for securing to the objective.

2. Medical instrument in accordance with claim 1, distinguished in that the guide is configured as a slit in a segment of the handle, where the handle in this segment at least partially surrounds the cross-section of a segment of the chisel, so that the chisel is guided in the slit secure from rotating.

3. Medical instrument in accordance with claim 2, distinguished in that a stop is configured on the guide that limits the strike length of the chisel.

4. Medical instrument in accordance with claim 2, distinguished in that a stop is configured on the chisel that limits the strike length of the chisel.

5. Medical instrument in accordance with claim 4, distinguished in that the stop is configured as an enlargement of the cross-section of the shaft of the chisel in the area of the guide in the direction of the handle or of the guide device.

6. Medical instrument in accordance with claim 4, distinguished in that the stop along the longitudinal axis of the shaft of the chisel is adjustable.

7. Medical instrument in accordance with claim 6, distinguished in that the stop restricts the strike length of the chisel by reduction.

8. Medical instrument in accordance with claim 2, distinguished in that the chisel can be driven in the working direction by means of a weight that can be slid on the shaft of the chisel, so that a stop as an abutment for the weight is formed on the shaft of the chisel.

9. Medical instrument in accordance with claim 8, distinguished in that at least the parts of the weight and/or the shaft of the chisel, which form a glide pair for sliding the weight along the chisel shaft, consist of materials with favorable gliding properties, particularly a low friction coefficient.

10. Medical instrument in accordance with claim 9, distinguished in that the outer contour of the weight, especially equipped with gripping surfaces, is ergonomically designed for facilitating operation of the instrument.

11. Medical instrument in accordance with claim 8, distinguished in that the stop that forms the abutment for the weight also forms the stop restricting the strike length of the chisel.

12. Medical instrument in accordance with claim 11 distinguished in that a soft-part protection capable of retracting tissue is installed on the handle.

13. Medical instrument in accordance with claim 1, distinguished in that the guide is configured as a guide device mounted on the handle, which device at least partially surround the cross-section of a segment of the chisel, so that the chisel is guided in the guide device.

14. Medical instrument in accordance with claim 13, distinguished in that at least the parts of the shaft of the chisel and/or of the guide, which form the glide parting for sliding the chisel, consist of materials with favorable gliding properties, especially a low friction coefficient.

15. Medical instrument in accordance with claim 14, distinguished in that the insertion depth of the chisel in the guide corresponds to a multiple of the height of the cross-section of the chisel.

16. Medical instrument in accordance with claim 15, distinguished in that the guide in its longitudinal and cross-section corresponds to the longitudinal and cross-section shape of the segment of the chisel taken up by the guide.

17. Medical instrument in accordance with claim 1, distinguished in that the enclosure device marking a target point of the chisel also forms a soft part protection which is capable of retracting tissue.

18. Medical instrument in accordance with claim 17, distinguished in that the enclosure device has a hammer platform for inserting the strike pin.

19. Medical instrument in accordance with claim 18, distinguished in that that at least all components coming directly into contact with the patient's body, especially bones and/or cartilage parts, are produced from materials tolerable for the body, especially tolerable steel alloys.

* * * * *